United States Patent [19]

Veber et al.

[11] Patent Number: 4,659,691

[45] Date of Patent: Apr. 21, 1987

[54] NOVEL CYCLIC HEXAPEPTIDE LHRH ANTAGONISTS

[75] Inventors: Daniel F. Veber, Ambler; Roger M. Freidinger, Hatfield, both of Pa.

[73] Assignee: Merck & Co., Inc., Rahway, N.J.

[21] Appl. No.: 699,778

[22] Filed: Feb. 8, 1985

[51] Int. Cl.$^4$ ............... A61K 37/43; C07K 5/12; C07K 7/20

[52] U.S. Cl. ................... 514/11; 514/800; 530/321; 530/313

[58] Field of Search ............... 260/112.5 R; 514/11, 514/800; 530/313, 321

[56] References Cited

U.S. PATENT DOCUMENTS

| 4,140,767 | 2/1979 | Veber | 260/112.5 S |
| 4,162,248 | 7/1979 | Strachan et al. | 260/112.5 S |
| 4,235,886 | 11/1980 | Freidinger et al. | 260/112.5 S |
| 4,310,518 | 1/1982 | Freidinger et al. | 260/112.5 S |
| 4,377,515 | 3/1983 | Veber et al. | 260/112.5 LH |

OTHER PUBLICATIONS

LHRH Peptides as Male & Female Contraceptives, Zatuchni, G.I., Shelton, J. D. and Sciarra, J. J., Editors Harper & Row, Phila., 1981, Chapter 3, pp. 24-36 & Chapter 5, pp. 46-62.
Int. J. Peptide Protein Res., vol. 23, pp. 142-150 (1984).
Donformationally Directed Drug Design; R. S. Struthers, et al., Vita, J. A. & Gordon, M., editors Amer. Chem. Soc. (1984) pp. 239-261.
J. Med. Chem., 17 pp. 1016-1019 (1974).
J. Med. Chem. 18, 1244-1247 (1975) by John P. Yardley et al.
Proc. Soc. Exp. Biol. Med. 152, pp. 29-32 (1976) by R. H. Rippel et al.
Proc. Soc. Expt'l Bio. and Med. vol. 152, pp. 432-436 (1976).
Nature, vol. 292, No. 5818, pp. 55-58 (1981).
J. Org. Chem. 38, pp. 2379-2383 (1973).
J. Med. Chem. 1979, vol. 22 (5) pp. 586-588.
Methods Enzymol 37, p. 82 (1975).
Khim. Prir. Soedin 1983 (3) pp. 398-399.
Science, vol. 218, pp. 160-162 (1982).
Peptides 1976 (Proceedings of the Fourteenth European Peptide Symposium, Wepion, Belgium, Apr. 11-17 (1976) pp. 427-436.
Science, vol. 210, pp. 656-658 (1980).
J. Med. Chem. 25, 795-801 (1982).
"Peptides, Structure and Function", Proceed of the 8th American Peptide Symposium, V. Hruby and D. Rich., Eds., Pierce Chemical Co., Rockford, Ill., 1983, p. 337.

Primary Examiner—Delbert R. Phillips
Attorney, Agent, or Firm—Robert J. North; Hesna J. Pfeiffer

[57] ABSTRACT

Novel peptides of the formula:

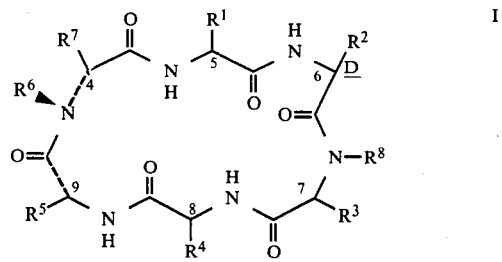

where $R^1$ through $R^8$ are various radicals derived from L- and D- amino acids; having LHRH antagonist activity; useful in reducing fertility.

Pharmaceutical compositions and methods for use in reducing fertility.

10 Claims, 2 Drawing Figures

NOVEL CYCLIC HEXAPEPTIDE LHRH ANTAGONISTS

BACKGROUND OF THE INVENTION

1. Field of the Invention

The present invention is concerned with novel peptide compounds having LHRH antagonist activity, and with pharmaceutical compositions containing said novel peptide compounds, as well as their use in methods of reducing fertility.

2. Brief Description of the Prior Art

Luteinizing hormone-releasing hormone (LHRH) is a neurohumoral hormone produced in the hypothalamus which stimulates the secretion of the pituitary hormones: luteinizing hormone (LH) and follicle-stimulating hormone (FSH), which in turn produce changes resulting in the induction of ovulation. LHRH has the following structure:

pyroGlu—His—Trp—Ser—Tyr—Gly—Leu—Arg—Pro—GlyNH$_2$

Synthetic replicates of LHRH were readily available shortly after the primary sequence was disclosed in 1971 and, as a result, a sizable number of structural analogs of LHRH have been made and tested over the last few years. Some of these have proved to be more potent than LHRH as well as long-acting. See Rivier et al., Peptides 1976 (Proceedings of the Fourteenth European Peptide Symposium, Wepion, Belgium, Apr. 11–17, 1976), pp. 427–436. Thus, a D-amino acid has been utilized in the 6-position and/or N-methyl-Leu$^7$ substitution has been made in order to obtain potent, long-acting LHRH agonists and antagonists.

A decapeptide analog of LH-RH containing a gamma-lactam as a conformational constraint is disclosed by R. M. Freidinger et al. of Merck & Co., Inc. in Science Vol. 210, pp. 656-8 (1980) and U.S. Pat. No. 4,377,515, hereby incorporated by reference. The analog was shown to be more active as an LH-RH agonist than the parent hormone and provides evidence for a bioactive conformation containing a Tyr$^5$-Gly$^6$-Leu$^7$-Arg$^8$ beta-turn.

Analog studies have also shown that the hydrophobic or basic D-amino acids in position 6 enhance potency. See Nestor, et al. J. Med. Chem. 25, 795 (1982) and Hocart et al., "Peptides, Structure and Function", Proceedings of the Eighth American Peptide Symposium, V. Hruby and D. Rich, Ed., Pierce Chemical Co., Rockford, Ill., 1983, p. 337.

Decapeptide LHRH antagonists have been disclosed; for example, see Science, vol. 218, pp. 160-2 (1982). Also, Khim. Prir. Soedin 1983 (3), pp. 398-9 (Russ.) by Burov S. V. et al. discloses cyclo [Pro-Ser-Tyr-D-Ala-Leu-Arg] as a contraceptive agent but no data is given.

An extensive amount of work has been carried out in the somatostatin agonist area as exemplified in Nature, Vol. 292, No. 5818, pp. 55-58 (1981), D. F. Veber et al., of Merck & Co., Inc.; U.S. Pat. No. 4,140,767 to D. F. Veber; U.S. Pat. No. 4,162,248 to R. G. Strachan et al.; U.S. Pat. No. 4,235,886 to R. M. Freidinger et al.; and U.S. Pat. No. 4,310,518 to R. M. Freidinger et al. all assigned to Merck & Co., Inc.

The above references describe, inter alia, highly active cyclic hexapeptide somatostatin analogs containing a beta turn.

Due to the tremendous interest created in developing a more potent and long lasting anti-fertility agent not having the adverse side effects associated with traditional estrogen and progestogen treatment, newer LH-RH antagonist agents are constantly being investigated.

SUMMARY OF THE INVENTION

It has been found that cyclic hexapeptides possessing a unique amino acid sequence and conformational structure, as applied to the LH-RH antagonist area, possess significant LH-RH antagonist activity.

The novel LH-RH antagonist cyclopeptides incorporate a beta turn conformation, a hydrophobic or basic D-amino acid in the corresponding LH-RH 6-position (as indicated in Structure I), a hydrophobic residue in corresponding position 9, and a secondary amino acid in position 4, which may also bear a hydrophobic side chain, for stabilizing the required and necessary beta turn. The resulting conformation also contains a cis-amide configuration between amino acid residues 4 and 9, as indicated in Structure I by the dotted lines, which is particularly favored by the secondary amino acid in position 4.

It is theorized that this novel structure provides a key portion of the biologically active (receptor bound) conformation of the peptide thus affording LHRH antagonist activity in a simplified structure.

In accordance with the present invention there is provided a novel peptide of the formula:

wherein:

$R^1$ is benzyl, p-hydroxybenzyl, 4-imidazolylmethyl or 3-indolylmethyl;

$R^2$ is a radical, derived from glycine or a D-amino acid, said radical selected from H, $C_1$-$C_4$ linear or branched alkyl, benzyl, halobenzyl, aminomethylbenzyl, $C_1$-$C_4$ alkylbenzyl, where the phenyl ring of the benzyl moieties may have 1-3 substitutents, $C_1$-$C_4$ alkoxybenzyl, trifluoromethylbenzyl, 3-quinolylmethyl, 1- or 2-naphthylmethyl, 4-imidazolylmethyl, $C_3$-$C_7$ cycloalkylmethyl, 3-(9,10-dihydro-9-anthryl)methyl, 3-(p-biphenylyl)methyl, 3-(2-fluorenyl)methyl, 3-(9-anthryl)methyl, 3-(benzhydryl)methyl, $(CH_2)_{2-4}$-$NH_2$ or $(CH_2)_{2-4}$-NH-C($=$NH)NH$_2$;

$R^3$ is H or $C_1$-$C_5$ linear or branched alkyl;

$R^4$ is $(CH_2)_{2-4}$-NH$_2$ or $(CH_2)_{2-4}$-NH C($=$NH)-NH$_2$;

$R^5$ is H, $C_1$-$C_4$ linear or branched alkyl, benzyl, halobenzyl, $C_1$-$C_4$ alkylbenzyl, where the phenyl ring of the benzyl moieties may have 1-3 substitutents, $C_1$-$C_4$ alkoxybenzyl, trifluoromethylbenzyl, 3-quinolylmethyl, 1- or 2-naphthylmethyl, 4-imidazolylmethyl, $C_3$-$C_7$ cycloalkylmethyl, 3-(9,10-dihydro-9-anthryl)methyl, 3-(p-biphenylyl)methyl, 3-(2-fluorenyl)methyl, 3-(9-anthryl)methyl, or 3-(benzhydryl)methyl;

$R^6$ is $C_1$-$C_4$ linear or branched alkyl;

$R^7$ is H, $C_1$-$C_4$ linear or branched alkyl, benzyl, halobenzyl, $C_1$-$C_4$ alkylbenzyl, where the phenyl ring of the benzyl moieties may have 1–3 substituents, $C_1$-$C_4$ alkoxybenzyl, trifluoromethylbenzyl, 3-quinolylmethyl, 1- or 2-naphthylmethyl, 4-imidazolylmethyl, $C_3$-$C_7$ cycloalkylmethyl, 3-(9,10-dihydro-9-anthryl)methyl, 3-(p-biphenylyl)methyl, 3-(2-fluorenyl)methyl, 3-(9-anthryl)methyl, or 3-(benzhydryl)methyl;

$R^8$ is H or methyl;

wherein $R^6$ and $R^7$ can jointly be alkylene, attached together to form —$(CH_2)_{3-4}$—; and wherein amino acid residues 4 and 9 are interconnected through a cis-amide structure; and pharmaceutically acceptable salts thereof. Further provided is a method of reducing fertility comprising administering to a patient in need of such treatment, a therapeutically effective amount of a compound as defined above. Preferably, said administering is accomplished orally.

Also provided is a pharmaceutical composition for use in reducing human fertility comprising a therapeutically effective amount of the compound as defined above, or pharmaceutically acceptable salts or esters thereof, in a pharmaceutically acceptable liquid or solid carrier. Preferably, the pharmaceutical composition is orally effective.

DESCRIPTION OF THE INVENTION AND PREFERRED EMBODIMENTS

Preferred embodiments of the subject compounds of the instant invention are best realized in the following structural formula:

I wherein:

$R^1$ is benzyl, p-hydroxybenzyl, 4-imidazolylmethyl or 3-indolylmethyl;

said $R^1$ values being derived from the L-amino acids: phenylalanine, tyrosine, histidine and tryptophan, respectively;

$R^2$ is a radical, derived from glycine or a D-amino acid, said radical selected from H, methyl, benzyl, 3-pyridylmethyl, 3-indolylmethyl, 3-quinolylmethyl, 2-naphthylmethyl, $(CH_2)_4NH_2$ or $(CH_2)_3NHC(=NH)NH_2$;

said $R^2$ values being derived from the following D-amino acids (excepting glycine); glycine, alanine, phenylalanine, 3-pyridylalanine, tryptophan, 3-quinolylalanine, 2-naphthylalanine, lysine and arginine; respectively;

$R^3$ is H or $C_1$-$C_5$ linear or branched alkyl;

said $R^3$ values being derived from the following L-amino acids: glycine, alanine, leucine, isoleucine or valine;

$R^4$ is $(CH_2)_4$-$NH_2$, $(CH_2)_3NH_2$, or $(CH_2)_3NHC(=NH)NH_2$;

said $R^4$ values being derived from the following L-amino acids; lysine, ornithine, or arginine, respectively;

$R^5$ is H, methyl, benzyl, m- or p-chlorobenzyl, m- or p-bromobenzyl, 1-naphthylmethyl, 2-naphthylmethyl, 3-indolylmethyl, 3-quinolylmethyl, 3-pyridylmethyl or 4-imidazolylmethyl;

said $R^5$ values being derived from the respective L-amino acids: glycine, alanine, phenylalanine, m- or p-chlorophenylalanine, m- or p-bromo-phenylalanine, 3-(1-naphthyl)alanine, 3-(2-naphthyl)-alanine, tryptophan, 3-quinolylalanine, 3-pyridylalanine or histidine; respectively;

$R^6$ is methyl or jointly alkylene with $R^7$;

$R^7$ is H, methyl, benzyl, m- or p-chlorobenzyl, m- or p-bromobenzyl, 1-naphthylmethyl, 2-naphthylmethyl, 3-indolylmethyl, 3-quinolylmethyl, 3-pyridylmethyl or 4-imidazolylmethyl; or jointly alkylene with $R^6$; and $R^8$ is H;

wherein $R^6$ and $R^7$ can jointly be alkylene, attached together to form —$(CH_2)_{3-4}$—; and wherein amino acid residues 4 and 9 are interconnected through a cis-amide structure;

said $R^6$ and $R^7$ values being simultaneously derived from the following L-amino acids: N-methylalanine, D-(N-methyl)alanine, proline, pipecolic acid, alpha N-methyltryptophan, sarcosine (N-methyl glycine) or N-methylphenylalanine, where $R^6$ and $R^7$ are joined together forming the amino acid cyclic radical from proline or pipecolic acid.

Other amino acids of the formula: $RCH(NH_2)COOH$ useful in producing the claimed cyclic hexapeptides claimed herein include the following where R is:

m- and p-chlorobenzyl;
m- and p-bromobenzyl;
m- and p-fluorobenzyl;
m- and p-methylbenzyl;
2,4-dimethylbenzyl;
o- and p-methoxybenzyl;
2,4,6-trimethylbenzyl;
p-$CF_3$benzyl;
cyclopropylmethyl;
cyclopentylmethyl;
cyclohexylmethyl;
p-aminomethylbenzyl; and the amino acids
2,4-diaminobutyric acid;
2-amino-4-guanidinobutyric acid;
2-amino-6-guanidinohexanoic acid;
N-methyl glycine, N-methyl leucine and the like.

It will be appreciated that the values of $R^1$-$R^8$ are specifically conditioned on the choice of specific amino acids for each respective position from those specifically enumerated above. Such choice leads to the specific configuration of Structure I in which the amino acid residues 4 and 9 vis-a-vis their alpha carbon atoms assume a cis configuration to each other in relation to the interconnecting amide bridge. This cis-amide bridging structure in Structure I is physically evidenced from proton nuclear magnetic resonance (NMR) data in which the attendant amino acid residue 4 and 9 alpha carbon hydrogen atoms exhibit nuclear Overhauser enhancement indicating their proximity in space.

Also the cis-amide structure is evident in proline-containing analogs from the $C^{13}$ NMR data showing the beta- and gamma-carbon shifts in the accepted ranges for cis-proline. See Douglas and Borey, *J. Org. Chem.* 38, pp. 2379-2383 (1973), hereby incorporated by reference for this purpose.

The β-turn encompassing positions 5-8 combined with the β-turn encompassing positions 8-9-4-5 with the cis-amide between positions 9 and 4 in the cyclic hexapeptides of the present invention allows proximity of side chains $R^2$ and $R^3$ and sidechains $R^5$ and $R^7$. This proximity is shown by the proton NMR data in which a γ-proton(s) of $R^3$ (where $R^3$ is $C_2$-$C_5$ alkyl) is shifted upfield relative to its normal position by the ring current of $R^2$ when $R^2$ is a hydrophobic aromatic group. This proximity is further shown by an upfield shift of a β-proton(s) of $R^7$ when $R^7$ is $C_1$-$C_5$ alkyl and $R_5$ is a hydrophobic aromatic group or by an upfield shift of a β-proton(s) of $R^5$ when $R^5$ is $C_1$-$C_5$ alkyl and $R^7$ contains a hydrophobic aromatic group. These side chain relationships are considered crucial for the LH-RH antagonist activity of the compounds of the present invention.

By the expression, "beta turn" is meant a reversal of the direction of the peptide backbone by 180° through four consecutive amino acid residues in the cyclic peptide. The "beta-turn" is especially favored by a D-amino acid at the second position of the tetrapeptide. Its significance in relation to the novel cyclohexapeptide compounds of the present invention and their use as LH-RH antagonists is that these compounds have been specifically designed for the tetrapeptide positions 5-8 to adopt a beta turn. Considerable experiental evidence favors this turn in the receptor bound ("active") conformation of LHRH.

Preferred compounds of the instant invention are where in the formula:

$R^1$ is p-hydroxybenzyl;
$R^3$ is isobutyl;
$R^4$ is $(CH_2)_3NH-C(=NH)NH_2$
$R^6$ is methyl or alkylene joined to $R^7$ methylene;
$R^7$ is methyl, benzyl, 3-indolylmethyl or alkylene joined to $R^6$;
$R^8$ is H.

A shorthand linear format for expressing the preferred structure is cyclo[Tyr-$AA^6$ Leu-Arg-$AA^9$-$AA^4$], or the cyclic structure:

where Tyr is tyrosine, Leu is leucine, Arg is arginine, $AA^4$, $AA^6$, $AA^9$ are generic symbols for the amino acid residues described above giving rise to the $R^2$, $R^5$, $R^6$, and $R^7$ radicals.

As is customary in the protein and peptide chemistry art, unless specified otherwise; an amino acid is presumed to be in the naturally ocurring L-configuration.

Preferred in the above formula as a subgenus is where $R^1$ is p-hydroxybenzyl, $R^3$ is isobutyl, $R^4$ is $(CH_2)_3NHC(=NH)NH_2$, and $R^6$ and $R^7$ are joined to form $-(CH_2)_3-$.

The subgenus depicted in shorthand form:
cyclo[Tyr-$AA^6$-Leu-Arg-$AA^9$-Pro].

Representative examples of the subject novel peptides expressed for convenience in the abbreviated linear format are:
cyclo[Tyr-D-Trp-Leu-Arg-Trp-N-Me-Ala]
cyclo[Tyr-D-Trp-Leu-Arg-Trp-N-Me-D-Ala]
cyclo[Tyr-D-Trp-Leu-Arg-Trp-N-Me-Abu]
cyclo[Tyr-D-Trp-Leu-Arg-Trp-Sar]
cyclo[Tyr-D-Trp-Leu-Arg-Trp-N-MePhe]
cyclo[Tyr-D-Trp-Leu-Arg-Trp-N-Me-Trp]
cyclo[Tyr-D-Trp-Leu-Arg-Ala-N-Me-Trp]
cyclo[Tyr-D-Trp-Leu-Arg-Trp-N-Me-D-Trp]
cyclo[Tyr-D-Trp-Leu-Arg-Ala-N-Me-D-Trp]
cyclo[Tyr-D-Ala-Leu-Arg-Trp-N-Me-Ala]
cyclo[Tyr-D-Ala-Leu-Arg-Trp-N-Me-D-Ala]
cyclo[Tyr-D-Ala-Leu-Arg-Trp-Pro]
cyclo[Tyr-D-Ala-Leu-Arg-Trp-N-Me-Abu]
cyclo[Tyr-D-Ala-Leu-Arg-Trp-Sar]
cyclo[Tyr-D-Ala-Leu-Arg-Trp-N-Me-Phe]
cyclo[Tyr-D-Trp-Leu-Arg-Phe-N-Me-Ala]
cyclo[Tyr-D-Trp-Leu-Arg-Phe-N-Me-D-Ala]
cyclo[Tyr-D-Trp-Leu-Arg-Phe-Pro]
cyclo[Tyr-D-Trp-Leu-Arg-Phe-N-Me-Abu]
cyclo[Tyr-D-Trp-Leu-Arg-Phe-Sar]
cyclo[Tyr-D-Trp-Leu-Arg-Phe-N-MePhe]
cyclo[Tyr-Gly-Leu-Arg-Trp-N-MeAla]
cyclo[Tyr-Gly-Leu-Arg-Trp-N-Me-D-Ala]
cyclo[Tyr-Gly-Leu-Arg-Trp-Pro]
cyclo[Tyr-Gly-Leu-Arg-Trp-N-Me-Abu]
cyclo[Tyr-Gly-Leu-Arg-Trp-Sar]
cyclo[Tyr-Gly-Leu-Arg-Trp-N-Me-Phe]
cyclo[Tyr-D-Arg-Leu-Arg-Trp-N-MeAla]
cyclo[Tyr-D-Arg-Leu-Arg-Trp-D-N-Me-Ala]
cyclo[Tyr-D-Arg-Leu-Arg-Trp-Pro]
cyclo[Tyr-D-Arg-Leu-Arg-Trp-N-Me-Abu]
cyclo[Tyr-D-Arg-Leu-Arg-Trp-Sar]
cyclo[Tyr-D-Arg-Leu-Arg-Trp-N-MePhe]
cyclo[Tyr-D-Arg-Leu-Arg-Trp-N-Me-Trp]
cyclo[Tyr-D-Arg-Leu-Arg-Ala-N-Me-Trp]
cyclo[Tyr-D-Arg-Leu-Arg-Trp-N-Me-D-Trp]
cyclo[Tyr-D-Arg-Leu-Arg-Ala-N-Me-D-Trp]
cyclo[Tyr-D-Phe-Leu-Arg-Trp-N-MeAla]
cyclo[Tyr-D-Phe-Leu-Arg-Trp-N-Me-DAla]
cyclo[Tyr-D-Phe-Leu-Arg-Trp-Pro]
cyclo[Tyr-D-Phe-Leu-Arg-Trp-N-MeAbu]
cyclo[Tyr-D-Phe-Leu-Arg-Trp-Sar]
cyclo[Tyr-D-Phe-Leu-Arg-Trp-N-MePhe]
cyclo[Tyr-D-3QAla-Leu-Arg-Trp-N-MeAla]
cyclo[Tyr-D-3QAla-Leu-Arg-Trp-N-Me-DAla]
cyclo[Tyr-D-3QAla-Leu-Arg-Trp-Pro]
cyclo[Tyr-D-3QAla-Leu-Arg-Trp-N-MeAbu]
cyclo[Tyr-D-3QAla-Leu-Arg-Trp-Sar]
cyclo[Tyr-D-3QAla-Leu-Arg-Trp-N-Me-Phe]
cyclo[Tyr-D-Lys-Leu-Arg-Trp-N-MeAla]
cyclo[Tyr-D-Lys-Leu-Arg-Trp-N-Me-D-Ala]
cyclo[Tyr-D-Lys-Leu-Arg-Trp-Pro]
cyclo[Tyr-D-Lys-Leu-Arg-Trp-N-Me-Abu]
cyclo[Tyr-D-Lys-Leu-Arg-Trp-Sar]
cyclo[Tyr-D-Lys-Leu-Arg-Trp-N-Me-Phe]
cyclo[Tyr-D-Lys-Leu-Arg-Trp-N-Me-Trp]

cyclo[Tyr-D-Lys-Leu-Arg-Ala-N-Me-Trp]
cyclo[Tyr-D-Lys-Leu-Arg-Trp-N-Me-D-Trp]
cyclo[Tyr-D-Lys-Leu-Arg-Ala-N-Me-D-Trp]
cyclo[Tyr-D-2N-Ala-Leu-Arg-Trp-N-MeAla]
cyclo[Tyr-D-2N-Ala-Leu-Arg-Trp-N-Me-DAla]
cyclo[Tyr-D-2N-Ala-Leu-Arg-Trp-Pro]
cyclo[Tyr-D-2N-Ala-Leu-Arg-Trp-N-Me-Abu]
cyclo[Tyr-D-2N-Ala-Leu-Arg-Trp-Sar]
cyclo[Tyr-D-2N-Ala-Leu-Arg-Trp-N-MePhe]
cyclo[Tyr-D-p-ClPhe-Leu-Arg-Trp-N-MeAla]
cyclo[Tyr-D-3-PyrAla-Leu-Arg-Trp-Pro]
cyclo[Phe-D-Trp-Leu-Arg-Trp-Pro]
cyclo[His-D-Trp-Leu-Arg-Trp-Pro]
cyclo[Tyr-D-Trp-Leu-Arg-Trp-Pro]
cyclo[Tyr-D-Trp-Gly-Arg-Trp-N-MeAla]
cyclo[Tyr-D-Trp-Ala-Arg-Trp-N-MeAla]
cyclo[Tyr-D-Trp-Leu-Arg-Trp-N-MeAla]
cyclo[Tyr-D-Trp-Ile-Arg-Trp-N-MeAla]
cyclo[Tyr-D-Trp-Val-Arg-Trp-N-MeAla]
cyclo[Tyr-D-Trp-Leu-Lys-Trp-N-MePhe]
cyclo[Tyr-D-Trp-Leu-Orn-Trp-N-MePhe]
cyclo[Tyr-D-Trp-Leu-Arg-2N-Ala-Pro]
cyclo[Tyr-D-Trp-Leu-Arg-1N-Ala-Pro]
cyclo[Tyr-D-Trp-Leu-Arg-3QAla-Pro]
cyclo[Tyr-D-Trp-Leu-Arg-m-BrPhe-Pro]
cyclo[Tyr-D-Trp-Leu-Arg-p-Br-Phe-Pro]
cyclo[Tyr-D-Trp-Leu-Arg-m-ClPhe-Pro]
cyclo[Tyr-D-Trp-Leu-Arg-p-ClPhe-Pro]

Preferred species include:
cyclo[Tyr-D-Trp-Leu-Arg-Trp-Pro]
cyclo[Tyr-D-Trp-Leu-Arg-Trp-N-MeAla]
cyclo[Tyr-D-Trp-Leu-Arg-Ala-N-Me-Trp]
cyclo[Tyr-D-Trp-Leu-Arg-Trp-N-Me-Trp]

Particularly preferred is cyclo[Tyr-D-Trp-Leu-Arg-Trp-Pro] where D-Trp is D-tryptophan and Pro is proline.

The term "$C_1$-$C_4$ alkyl or $C_1$-$C_5$ alkyl" when used in the instant application is intended to represent those alkyl groups either straight or branched chain, which have from 1-4 or 1-5 carbon atoms respectively. Examples of such alkyl groups are methyl, ethyl, propyl, iso-propyl, butyl, sec-butyl, pentyl, isopentyl and the like.

In the instant compounds there are several asymmetric centers which will lead to the existence of isomers for such compounds. In the instant invention, for each of the asymmetric centers of the various amino acids which make up the instant cyclic hexapeptides, the intended L configurations intended to be encompassed are specifically set forth, except for amino acid residue 6, which is preferred in the D configuration.

The cyclic peptides of the instant invention as set forth by Structure I can exist as the neutral compound and also in the form of a pharmaceutically acceptable salt.

The pharmaceutically acceptable salts of the compounds of Structure I include the conventional non-toxic salts or the quaternary ammonium salts of the compounds of Formula I formed, e.g., from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, p-aminobenzoic, p-acetamidobenzoic, methanesulfonic, ethane disulfonic, oxalic, isethionic, and the like.

In the instant application several abbreviated designations are used for the amino acid components, certain preferred protecting groups, reagents and solvents. The meanings of such abbreviated designations are given in Table I.

TABLE I

| Abbreviated Designation | |
|---|---|
| | Amino Acid |
| AA | Amino Acid |
| Gly | Glycine |
| D-Arg- | D-arginine |
| D-3QAla | D-3(3-quinolyl)alanine |
| D-2N—Ala | D-3-(2-naphthyl)alanine |
| D-3-PyrAla | D-3-(3-pyridyl)alanine |
| Ala | L-alanine |
| Leu | L-leucine |
| Ile | L-isoleucine |
| Val | L-valine |
| Orn | L-ornithine |
| p-ClPhe | L-p-chlorophenylalanine |
| 1-NAla | L-3-(1-naphthyl)alanine |
| p-FPhe | L-p-fluorophenylalanine |
| N—MeAla | L-N—methylalanine |
| D-N—MeAla | D-N—methylalanine |
| N—MeAbu | L-N—methyl-alpha-aminobutyric acid |
| Sar | L-sarcosine |
| N—MePhe | L-N—methylphenylalanine |
| Lys | L-lysine |
| Phe | L-phenylalanine |
| Trp | L-tryptophan |
| D-Trp | D-tryptophan |
| Tyr | L-tyrosine |
| Val | L-valine |
| Pro | L-proline |
| | Protecting Groups |
| INOC | isonicotinyloxycarbonyl |
| BOC | tert-butyloxycarbonyl |
| OMe | methyl ester |
| Bu | tert-butyl |
| CBZ | benzyloxycarbonyl |
| Bzl | benzyl |
| 2-Cl—CBZ | 2-chlorobenzyloxycarbonyl |
| Acm | acetamidomethyl |
| Me | methyl |
| | Activating Groups |
| ONp | p-nitrophenyl ester |
| | Reagents or Solvents |
| TFA | Trifluoroacetic acid |
| TEA | Triethylamine |
| DMF | Dimethylformamide |

The novel cyclic LH-RH antagonists are prepared by cyclizing the corresponding linear peptides which are prepared by using the conventional Merrifield solid phase sequential synthesis technique. The process comprises (a) preparing a corresponding blocked linear peptide attached to a solid phase resin; (b) selectively deblocking the N-terminal amine group; (c) removing the linear peptide from the resin; (d) treating the linear peptide with a cyclizing agent to obtain the cyclic hexapeptide through the formation of an amide bond; (e) removing any side chain deblocking groups.

When the linear peptide is prepared on the resin, it is generally not critical which amino acid is selected to be at the C-terminal position provided only that the sequence of amino acids in the linear peptide corresponds to that in the desired LH-RH cyclohexapeptide of the instant invention. Once a linear peptide has been cyclized one can no longer determine which amino acid was at the C-terminus of the linear peptide.

While generally the selection of the first amino acid to start the chain is not critical, since the linear peptide will be cyclized, there may be other factors which may prefer one starting amino acid over another. For example D-Trp can react with t-butyl carbonium ions which are formed when BOC groups are removed. Thus, selection of a reaction sequence which places D-Trp at the N-terminal end of the linear peptide will cause D-Trp to be added last, and thus it will have the least exposure to t-butyl carbonium ions. This type of selection may not always be possible, such as where there are two indole containing moieties in the peptide. However, such reaction sensitivities should be considered when planning a peptide reaction sequence.

The synthesis of the linear peptides by the solid phase technique is conducted in a stepwise manner on chloromethylated resin. The resin is composed of fine beads (20-70 microns in diameter) of a synthetic resin prepared by copolymerization of styrene with 1-2 percent divnylbenzene. The benzene rings in the resin are chloromethylated in a Friedel-Crafts reaction with chloromethyl methyl ether and stannic chloride. The Friedel-Craft reaction is continued until the resin contains 0.5 to 5 mmoles of chlorine per gram of resin.

The amino acid selected to be the C-terminal amino acid of the linear peptide is converted to its amino protected derivative. The carboxyl group of the selected C-terminal amino acid is bound covalently to the insoluble polymeric resin support, as for example, as the carboxylic ester of the resin-bonded benzyl chloride present in chloromethyl-substituted polystyrene-divinylbenzene resin. After the amino protecting group is removed, the amino protected derivative of the next amino acid in the sequence is added along with a coupling agent, such as dicyclohexylcarbodiimide. The amino acid reactant may be employed in the form of a carboxyl-activated amino acid such as the ONp ester, an amino acid azide, and the like. Deprotection and addition of successive amino acids is performed until the desired linear peptide is formed.

The selection of protecting groups is, in part, dictated by particular coupling conditions, in part by the amino acid and peptide components involved in the reaction.

Amino-protecting groups ordinarily employed include those which are well known in the art, for example, urethane protecting substituents such as benzyloxycarbonyl(carbobenzoxy), p-methoxycarbobenzoxy, p-nitrocarbobenzoxy, t-butyloxycarbonyl, and the like. It is preferred to utilize t-butyloxycarbonyl (BOC) for protecting the α-amino group in the amino acids undergoing reaction at the carboxyl end of said amino acid. The BOC protecting group is readily removed following such coupling reaction and prior to the subsequent step by the relatively mild action of acids (i.e. trifluoro acetic acid, or hydrogen chloride in ethyl acetate).

The OH group of Tyr can be protected by the Bzl group and the end amino group of Lys or Orn can be protected by the INOC group or the 2-chlorobenzyloxycarbonyl (2-Cl-CBZ) group. In the case of Lys, it is preferred to protect the alpha-amino group with 2-Cl-CBZ group as this group is removed simultaneously with the Bzl groups by treatment with HF after the linear peptide has been cyclized. The INOC group is not removed by HF and requires an additional treatment with Zn. Neither group is affected by TFA, used for removing BOC protecting groups. After the linear peptide is cyclized, the protective groups, such as 2-Cl-CBZ and Bzl, are removed by treatment with HF.

After the linear peptide hwas been formed on the solid phase resin, it may be removed from the resin by a variety of methods which are well known in the art. For example the peptide may be cleaved from the resin with hydrazine and thus directly form the peptide hydrazide which may be subsequently cyclized via the azide to the desired cyclic peptide. The hydrazide is converted to the corresponding azide by reaction with a reagent which furnishes nitrous acid in situ. Suitable reagents for this purpose include a lower alkyl nitrite (e.g. t-butyl nitrite, isoamyl nitrite) or an alkali metal nitrite salt (e.g., sodium nitrite, potassium nitrite) in the presence of a strong acid such as hydrochloric, phosphoric, etc. This reaction is carried out in the presence of either water and/or a non-aqueous solvent such as dimethylformamide, tetrahydrofuran, dioxane, chloroform, methylene chloride, etc., at a temperature between about −40° C. and +20° C. Alternatively, the peptide may be removed from the resin by treatment with a lower alcohol such as methanol in the presence of an organic base such as triethylamine, thus resulting in the formation of the corresponding lower alcohol ester of the linear peptide. The resulting ester may be converted to the hydrazide which may then be cyclized, via the azide, to the desired cyclic peptide. The preferred method for cleaving the peptide from the resin in the present invention is the use of methanol and triethylamine.

As reference Table II will show, one preferred overall procedure for preparing the desired cyclic peptides of the present invention involves the stepwise synthesis of the linear peptide on a solid phase resin. More specifically, in the process for preparing:

the carboxyl end of the N-blocked amino acid proline is bound covalently to an insoluble polymeric resin support as the carboxylic acid ester of the resin-bonded benzyl chloride. The amino group of Pro is protected by the BOC group. After the attachment of the Pro is completed on the resin, the protecting group BOC is removed by treatment with TFA in CH$_2$Cl$_2$. The subsequent amino acids are attached, in the form of BOC-amino acid, using DCCI (dicyclohexylcarbodiimide) as the condensing agent or an active ester such as ONp. After the desired linear peptide has been prepared, the N-terminal amino group is selectively deblocked and the peptide is removed from the resin by treatment with methanol and triethylamine. The resulting linear peptide ester with the N-terminal amino group deblocked having the amino acid sequence:

is treated with sodium hydroxide in dioxane-water to form the corresponding acid. The acid is treated with diphenylphosphorylazide in DMF solvent and diisopropylethylamine. The linear peptide cyclizes to form:

During the cyclization the pH is checked and maintained at neutral by the addition of organic base. The "pH" in organic solvent is determined by the application of an aliquot of the solution to moistened narrow range pH paper.

After the linear peptide is cyclized, the protective group, OBzl, is removed by treatment with HF in the presence of anisole. The crude cyclic peptide obtained is purified chromatographically, preferably with column chromatography on silica gel. The elution solvent is generally an organic solvent or mixtures thereof which is selected by analyzing aliquots of the material using thin layer chromatography.

TABLE II

The reaction scheme for the preparation of one of the cyclic hexapeptides of this invention is outlined in the following series of reactions:

In accordance with the present invention there is also provided a method of reducing fertility comprising administering to a patient in need of such treatment, a therapeutically effective amount of a novel cyclic peptide of the formula described hereinabove.

Dosage levels of the order of 0.5 mg to 500 mg. per day are useful in the treatment of the above indicated conditions. For example, fertility is reduced by the administration of from about 10 microgram to about 7.5 mg. of the peptide per kilogram of body weight per day. Advantageously, from about 0.02 mg. to about 2 mg. per kilogram of body weight and especially from about 0.03 mg. to about 1 mg./kg. per daily dosage produce highly effective results.

The amount of active ingredient that may be combined with the carrier materials to produce a single dosage form will vary depending upon the host treated and the particular mode of administration. For example, a formulation intended for the oral administration of humans may contain from 5 mg. to 1 gram of active agent compounded with an appropriate and convenient amount of carrier material which may vary from about 5 to about 95 percent of the total composition. Dosage unit forms will generally contain between from about 25 mg. to about 500 mg. of active ingredient.

It will be understood, however, that the specific dose level for any particular patient will depend upon a variety of factors including the activity of the specific compound employed, the age, body weight, general health, sex, diet, time of administration, route of administration, rate of excretion, and drug combination.

In accordance with the present invention there is further provided pharmaceutical compositions for use in reducing fertility. The novel peptides of the present invention possess a significant degree of LHRH antagonist activity.

For these purposes the novel peptides of the present invention may be administered orally, topically, parenterally, by inhalation spray, intravaginally, or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, dogs, cats, etc., the peptides of the present invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide a pharmaceutically elegant and palatable preparation. Tablets contain the active ingredient in admixture with non-toxic pharmaceutically acceptable excipients which are suitable for manufacture of tablets. These excipients may be, for example, inert diluents, such as calcium carbonate, sodium carbonate, lactose, calcium phosphate or sodium phosphate; granulating and disintegrating agents, for example maize starch, or alginic acid; binding agents, for example, starch, gelatine or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate alone or with a wax may be employed.

Formulations for oral use may also be presented as hard gelatine capsules wherein the active ingredient is mixed with an inert solid diluent, for example, calcium carbonate, calcium phosphate or kaolin, or as soft gelatine capsules wherein the active ingredient is mixed with water or an oil medium, for example arachis oil, peanut oil, liquid paraffin or olive oil.

Aqueous suspensions contain the active materials in admixture with excipients suitable for the manufacture of aqueous suspensions. Such excipients are suspending agents, for example sodium carboxymethyl-cellulose, methylcellulose, hydroxypropylmethylcellulose, sodium alginate, polyvinylpyrrolidone, gum tragacanth and gum acacia; dispersing or wetting agents may be a natural-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol mono-oleate, or condensation products of ethylene oxide with partial esters derived from fatty acid anhydrides and hexitol, for example polyoxyethylene sorbitan monooleate. The said aqueous suspensions may also contain one or more preservatives, for example, ethyl or n-propyl p-hydroxy benzoate, one or more coloring agents, one or more flavoring agents and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oil suspension may contain a thickening agent, for example beeswax, hard paraffin or cetyl alcohol. Sweetening agents, such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soya bean lecithin, and esters or partial esters derived from fatty acid anhydrides and hexitol, for example sorbitan mono-oleate, and condensation products of the said partial esters with ethylene oxide, for example polyoxyethylene sorbitan mono-oleate. The emulsions may also contain sweetening and flavouring agents. Syrups and elixirs may be formulated with sweetening agents, for example glycerol, sorbitol or sucrose. Such formulations may also contain a demulcent, a preservative and flavouring and coloring agents. The pharmaceutical compositions may be in the form of a sterile injectable preparation, for example as a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxid parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectibles.

The peptides of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are coca butter and polyethylene glycols.

The novel peptides of the present invention, with respect to the various amino acid substituents of the peptide, are prepared in accordance with well-known methods in the art for the synthesis of peptides.

The following Examples are given to illustrate the methods used to carry out the present invention. It is to be understood that the Examples are given for purposes of illustration and not limitation.

EXAMPLE 1

Step 1: Preparation of
H-Tyr(Bzl)-D-Trp-Leu-Arg-Trp-Pro-OCH$_2$ (2)

The novel peptide was prepared by standard Merrifield solid-phase methodology as described in J. Med. Chem., 1979, Vol. 22 (5), pp. 586–588, hereby incorporated by reference for this particular purpose, using a Beckman Model 990 peptide synthesizer to carry out all of the operations. The starting polymer was Boc-Pro esterified to 2% cross-linked polystyrenedivinylbenzene (2 mmol). The N$^\alpha$-Boc derivatives of Trp, Arg (HCl), Leu, D-Trp and Tyr (Bzl) were coupled using dicyclohexylcarbodiimide. Two couplings of 30 min. each (2.5 equiv. of Boc amino acid) were used for each amino acid. Trifluoroacetic acid (25% in CH$_2$Cl$_2$) was used for removal of the Boc protecting group. The detailed schedule for the solid-phase procedure is given in Table III, with program 1 used for the first coupling and program 2 for the second coupling. Solvents and volumes for the protected amino acids are given in Table IV. The finished peptide resin was dried in vacuo (3.4 g). The peptidoresin (3.2 g) was suspended in 126 ml of MeOH, and 14 ml of triethylamine was added. The mixture was stirred for 23 hours. The spent resin was removed by filtration and washed with a small volume of MeOH, and the combined filtrates were taken to dryness in vacuo. This treatment of the resin was repeated. Combined yield, 2.22 g (114%). TLC Rf (silica gel G, Analtech, 80:25:5 CHCl$_3$-MeOH-NH$_3$) 0.40. The crude product 2 was taken directly to the saponification in Step 2 without purification.

TABLE III

Schedule of Steps for 2 mmol Run

| step | solvent/reagent | vol, mL | mix time, min. |
|---|---|---|---|
| program 1 | | | |
| 1 | CHCl$_3$ | 2 × 40 | 5 |
| 2 | 25% TFA in CH$_2$Cl$_2$ | 1 × 40 | 2 |
| 3 | 25% TFA in CH$_2$Cl$_2$ | 1 × 40 | 25 |
| 4 | CHCl$_3$ | 3 × 40 | 2 |

TABLE III-continued

Schedule of Steps for 2 mmol Run

| step | solvent/reagent | vol, mL | mix time, min. |
|---|---|---|---|
| 5 | 10% TEA in CH$_2$Cl$_2$ | 2 × 40 | 5 |
| 6 | CHCl$_3$ | 3 × 40 | 2 |
| 7 | CH$_2$Cl$_2$ | 3 × 40 | 2 |
| 8 | Boc-AA | | 5 |
| 9 | 0.5 M DCC in CH$_2$Cl$_2$ | 10 | 5 |
| 10 | coupling | | 30 |
| 11 | DMF | 2 × 40 | 2 |
| 12 | MeOH | 1 × 40 | 2 |
| 13 | DMF | 1 × 40 | 2 |
| 14 | MeOH | 1 × 40 | 2 |
| 15 | CHCl$_3$ | 2 × 40 | 2 |
| program 2 | | | |

Repeat steps 4 (1×) to 15 of program 1

TABLE IV

| protected amino acid | solvent |
|---|---|
| Boc-Trp | 14 ml of CH$_2$Cl$_2$, 11 ml DMF |
| Boc-Arg(HCl) | 25 ml of DMF |
| Boc-Leu | 25 ml of CH$_2$Cl$_2$ |
| Boc-D-Trp | 11 ml of DMF |
| | 14 ml of CH$_2$Cl$_2$ |
| Boc-Tyr(Bzl) | 25 ml of CH$_2$Cl$_2$ |

Step 2: Preparation of H-Tyr(Bzl)-D-Trp-Leu-Arg-Trp-Pro-OH (3)

The ester 2 (1 g) was dissolved in a mixture of 50 ml dioxane (filtered through Alumina) and 50 ml water. 0.75N NaOH was added gradually such that the pH of the reaction mixture remained below 12.6. Complete saponification required 7 hours. The pH was adjusted to 6 with 1N HCl and water and dioxane were removed by lyophilization. The crude product 3 (TLC R$_f$ 0.27, Analtech Silica Gel G, 80:25:5 CHCl$_3$-MeOH-H$_2$O) was taken directly to the cyclization Step 3 without purification.

Step 3: Preparation of cyclo-[Tyr-(Bzl)-D-Trp-Leu-Arg-Trp-Pro] (4)

Hexapeptide amino acid 3 (0.81 g, 0.77 mmol) was dissolved in 500 ml of degassed DMF and the pH was adjusted to 7.4 (as measured by moistened pH sticks) with diisopropylethyl amine (0.135 ml, 0.77 mmol). Diphenylphosphoryl azide (0.47 g, 1.71 mmol) was added after the mixture had been cooled to −25°. The pH was maintained with additional small aliquots of i-Pr$_2$NEt. After two days, the mixture was warmed to 5° and after three days, to room temperature. The mixture was concentrated in vacuo after four days. The residue was triturated with water then dissolved in methylene chloride. This solution was washed with water then concentrated to a gummy residue (1.15 g), TLC R$_f$ 0.44 (Analtech Silica Gel G, 80:25:5 CHCl$_3$-MeOH-H$_2$O). The crude cyclic product 4 was taken directly to hydrogenolysis in Step 4 without purification.

Step 4: Preparation of cyclo-(Tyr-D-Trp-Leu-Arg-Trp-Pro) (5)

Figure 1:
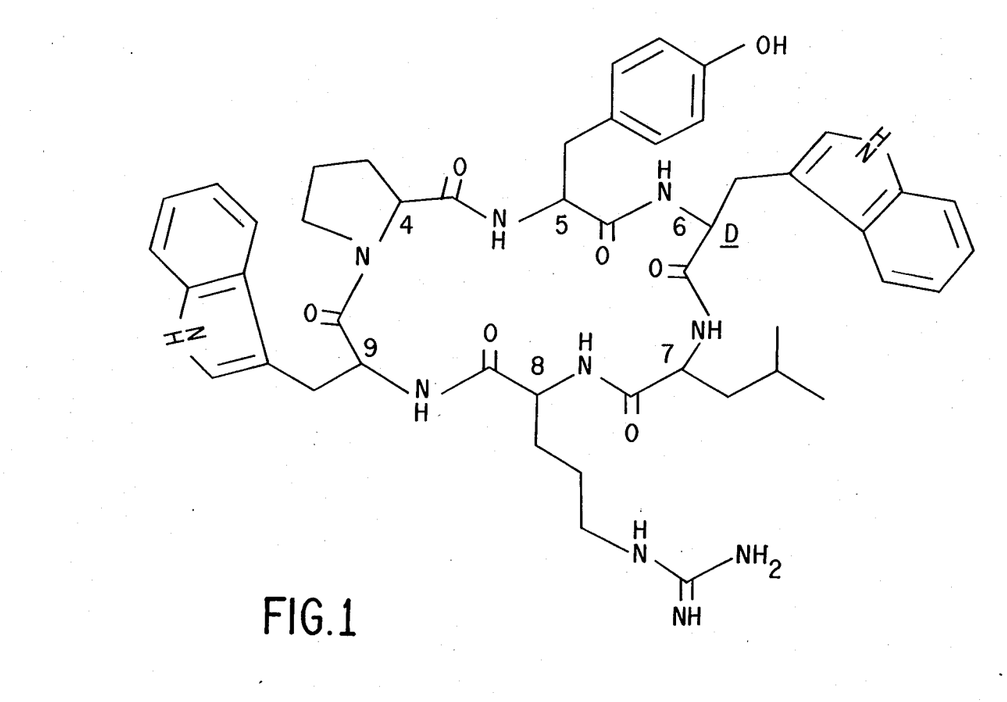
FIG. 1 illustrates a structural representation of cyclo[Tyr-D-Trp-Leu-Arg-Trp-Pro] in which the numbers inside the ring, analogous to Structure I, correspond to the analogous amino acid sequence in LHRH. The configurational character is indicated for D-amino acid residue 6 as well as the cis-amide interconnecting structure between amino acid residues 4 and 9, and the particular configuration for $R^6$ is shown.
Figure 2:
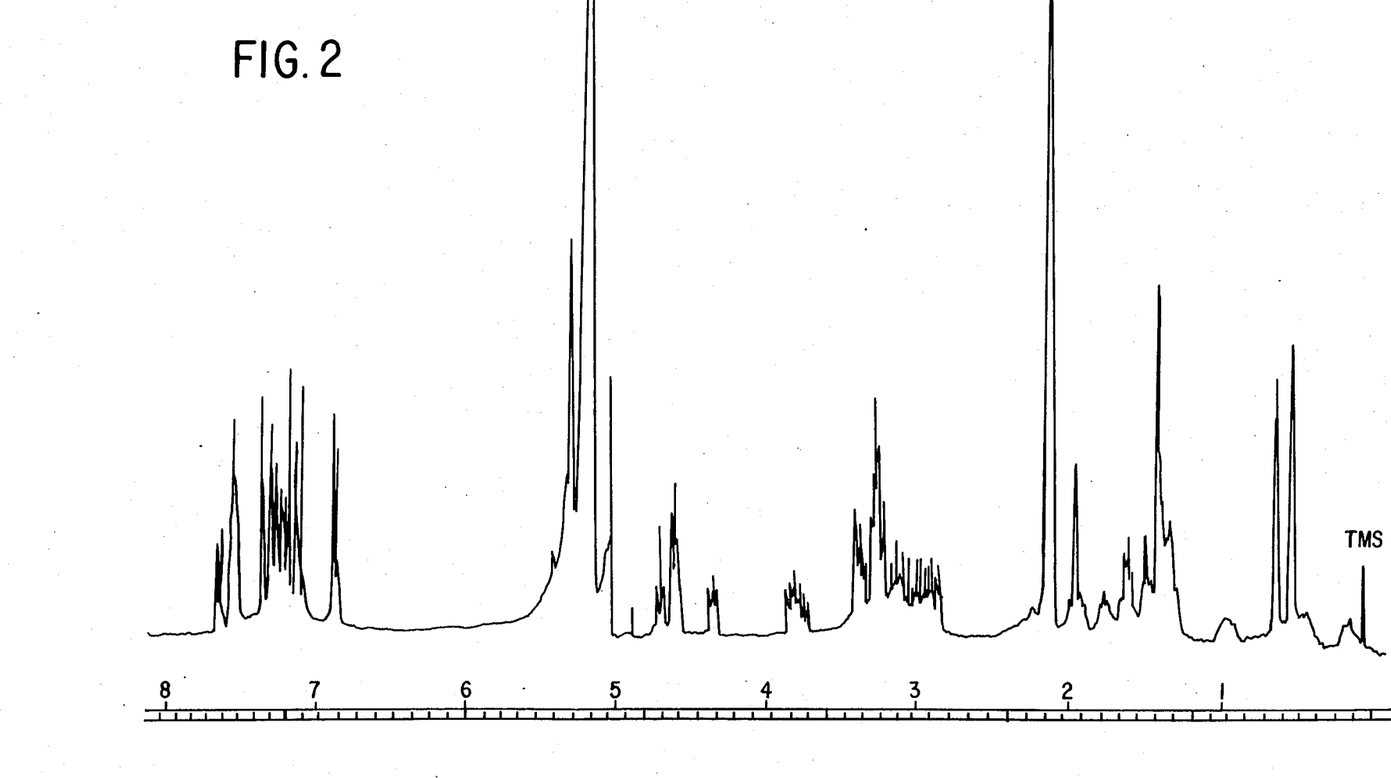
FIG. 2 is the NMR spectrum of cyclo[Tyr-D-Trp-Leu-Arg-Trp-Pro] taken in 100% $D_2O$ plus 5–8 drops HOAc-$d_4$ at 300 MHz, using tetramethylsilane (TMS) internal standard.

The product cyclic hexapeptide 4 (1 g) was dissolved in 45 ml of ethanol, 3 ml of acetic acid, and 2 ml of water and 840 mg of 10% Pd/C catalyst was added. After the reaction had been opened twice and was not complete, an additional 0.8 g of catalyst with 5 ml ethanol, 2 ml acetic acid, and 0.5 ml water was added. After two days, the mixture was filtered, and the filtrate was evaporated to a small volume. The residue was dissolved in 50% aqueous acetic acid and chromatographed on Sephadex G25SF. The three most pure column fractions were combined and concentrated in vacuo. The residue was dissolved in dilute aqueous acetic acid and lyophilized to provide 63 mg of product; TLC R$_f$0.15 (Analtech Silica Gel G, 80:25:5 CHCl$_3$-MeOH-H$_2$0), R$_f$0.55 (13:2:5 n-BuOH-HOAc-H$_2$O), R$_f$0.35 (15:5:1:2 EtOAc-pyridine-HOAc-H$_2$O). HPLC purity, 86%. Amino acid analysis, Arg (0.98), Pro (0.97), Leu (1.04), Tyr (1.02). The NMR spectrum in D$_2$O with 5–8 drops of HOAc-d$_4$ at 300 MHz illustrated in FIG. 2 is consistent with expected conformation and structure of 5.

EXAMPLE 2

Isolated Rat Pituitary Cell Culture System

Cyclic hexapeptides of the present invention are evaluated as antagonists of LH-RH in an in vitro pituitary cell culture system. This assay system is described in Vale and Brant, *Methods Enzymol*, 37, 82 (1975), hereby incorporated by reference for this purpose.

For purposes of illustration, the data for cyclo-[Tyr-D-Trp-Leu-Arg-Trp-Pro] (5) in this assay are presented. At a dose of $10^{-7}$M, compound 5 does not affect LH release.

At a dose range of $10^{-5}$ to $10^{-9}$M, compound 5 was tested in combination with a single dose of LHRH (luteinizing hormone release hormone) on rat pituitary cells in vitro for 60 minutes. The doses of LHRH used ranged from $10^{-6}$ to $10^{-10}$M. In this experiment, compound 5 was significantly antagonistic at a dose of $10^{-5}$M to LHRH at a concentration of $10^{-6}$, $5\times10^{-7}$, $5\times10^{-8}$, $10^{-8}$, $5\times10^{-9}$, $10^{-9}$, and $5\times10^{-10}$M. Molar concentrations of $10^{-7}$, $10^{-8}$ and $10^{-9}$ significantly reduced LH release in the presence of $10^{-6}$M LHRH. All lower doses of compound 5 were essentially ineffective in reducing LH release in the presence of $5\times10^{-7}$, $10^{-7}$, $5\times10^{-8}$ and $10^{-8}$M LHRH.

A significant dose related inhibition was obtained with compound 5 in the presence of $5\times10^{-9}$, $10^{-9}$ and $5\times10^{-10}$M LHRH. The greatest antagonism was observed in the presence of $10^{-9}$M LHRH. Application of conventional Schild transformation techniques yields an essentially linear plot, with a pA$_2$ of $1.78\times10^{-8}$M. The pA$_2$ is the negative logarithm of the molar concentration of compound 5 which reduces the effects of a dose of LHRH to that of half the dose.

It can be concluded that compound 5 is antagonistic to LHRH, and exhibits the greatest antagonistic effect at lower doses of LHRH.

What is claimed is:

1. A cyclic hexapeptide compound having the formula:

wherein:

$R^1$ is benzyl, p-hydroxybenzyl, 4-imidazolylmethyl or 3-indolylmethyl;

$R^2$ is a radical, derived from glycine or a D-amino acid, said radical selected from H, $C_1$-$C_4$ linear or branched alkyl, benzyl, halobenzyl, aminomethylbenzyl, $C_1$-$C_4$ alkylbenzyl, where the phenyl ring of the benzyl moieties can have 1-3 substituents, $C_1$-$C_4$ alkoxybenzyl, trifluoromethylbenzyl, 3-quinolylmethyl, 1- or 2-naphthylmethyl, 3-pyridylmethyl, 4-imidazolylmethyl, $C_3$-$C_7$ cycloalkylmethyl, 3-(9,10-dihydro-9-anthryl)methyl, 3-(p-biphenylyl)methyl, 3-(2-fluorenyl)methyl, 3-(9-anthryl)methyl, 3-(benzhydryl)methyl, $(CH_2)_{2\text{-}4}$-$NH_2$ or $(CH_2)_{2\text{-}4}$-NHC(=NH)NH_2$;

$R^3$ is H or $C_1$-$C_5$ linear or branched alkyl;

$R^4$ is $(CH_2)_{2\text{-}4}$-$NH_2$ or $(CH_2)_{2\text{-}4}$-NH C(=NH)-NH_2$;

$R^5$ is H, $C_1$-$C_4$ linear or branched alkyl, benzyl, halobenzyl, $C_1$-$C_4$ alkylbenzyl, where the phenyl ring of the benzyl moieties can have 1-3 substituents, $C_1$-$C_4$ alkoxybenzyl, trifluoromethylbenzyl, 3-quinolylmethyl, 3-pyridylmethyl, 1- or 2-naphthylmethyl, 4-imidazolylmethyl, $C_3$-$C_7$ cycloalkylmethyl, 3-(9,10-dihydro-9-anthryl)methyl, 3-(p-biphenylyl)methyl, 3-(2-fluorenyl)methyl, 3-(9-anthryl)methyl, or 3-(benzhydryl)methyl;

$R^6$ is $C_1$-$C_4$ linear or branched alkyl;

$R^7$ is H, $C_1$-$C_4$ linear or branched alkyl, benzyl, halobenzyl, $C_1$-$C_4$ alkylbenzyl, where the phenyl ring of the benzyl moieties can have 1-3 sbstituents, $C_1$-$C_4$ alkoxybenzyl, trifluoromethylbenzyl, 3-quinolylmethyl, 1- or 2-naphthylmethyl, 4-imidazolylmethyl, 3-indolylmethyl, $C_3$-$C_7$ cycloalkylmethyl, 3-(9,10-dihydro-9-anthryl)methyl, 3-(p-biphenylyl)methyl, 3-(2-fluorenyl)methyl, 3-(9-anthryl)methyl, or 3-(benzhydryl)methyl;

$R^8$ is H or methyl;

wherein $R^6$ and $R^7$ can also jointly be alkylene, attached together to form —$(CH_2)_{3\text{-}4}$—; and wherein amino acid residues 4 and 9 are interconnected through a cis-amide structure; and pharmaceutically acceptable salts thereof.

2. The compound according to claim 1 wherein:

$R^1$ is benzyl, p-hydroxybenzyl, 4-imidazolylmethyl or 3-indolylmethyl;

$R^2$ is a radical, derived from glycine or a D-amino acid, said radical selected from H, methyl, benzyl, p-chlorobenzyl, 3-pyridylmethyl, 3-indolylmethyl, 3-quinolylmethyl, 2-naphthylmethyl, $(CH_2)_4NH_2$ or $(CH_2)_3NHC(=NH)NH_2$;

$R^3$ is H or $C_1$-$C_5$ linear or branched alkyl;

$R^4$ is $(CH_2)_4$-$NH_2$, $(CH_2)_3NH_2$ or $(CH_2)_3NHC(=NH)NH_2$;

$R^5$ is H, methyl, benzyl, m- or p-chlorobenzyl, m- or bromobenzyl, 1-naphthylmethyl, 2-naphthylmethyl, 3-indolylmethyl, 3-quinolylmethyl, 3-pyridylmethyl or 4-imidazolylmethyl;

$R^6$ is methyl or jointly alkylene with $R^7$;

$R^7$ is H, methy, benzyl, m- or p-chlorobenzyl, m- or bromobenzyl, 1-naphthylmethyl, 2-naphthylmethyl, 3-indolylmethyl, 3-quinolylmethyl, 3-pyridylmethyl or 4-imidazolylmethyl; or jointly alkylene with $R^6$; and $R^8$ is H.

3. The compound according to claim 2 wherein:

$R^1$ is p-hydroxybenzyl;

$R^3$ is isobutyl;

$R^4$ is $(CH_2)_3NHC(=NH)NH_2$;

$R^6$ and $R^7$ are joined together to form —$(CH_2)_3$—.

4. The compound according to claim 3 wherein $R^5$ is 3-indolylmethyl.

5. The compound according to claim 3 wherein $R^2$ is 3-indolylmethyl.

6. The compound according to claim 1 which is: cyclo-[Tyr-D-Trp-Leu-Arg-Trp-Pro].

7. The compound according to claim 1 which is selected from:
cyclo[Tyr-D-Trp-Leu-Arg-Trp-N-Me-Ala],
cyclo[Tyr-D-Trp-Leu-Arg-Ala-N-Me-Trp], or
cyclo[Tyr-D-Trp-Leu-Arg-Trp-N-Me-Trp].

8. A method of reducing fertility comprising administering to a patient in need of such treatment, a therapeutically effective amount of a compound as defined in claim 1.

9. The method of claim 8 wherein said method of administering is oral.

10. A pharmaceutical composition for use in reducing human fertility comprising a therapeutically effective amount of the compound as defined in claim 1, or pharmaceutically acceptable salts or esters thereof, in a pharmaceutically acceptable liquid or solid carrier.

* * * * *